(12) United States Patent
Nicholas et al.

(10) Patent No.: US 8,895,793 B2
(45) Date of Patent: Nov. 25, 2014

(54) PROCESS FOR THE REDUCTION OF GASOLINE BENZENE CONTENT BY ALKYLATION WITH DILUTE ETHYLENE

(75) Inventors: Christopher P. Nicholas, Evanston, IL (US); Alakananda Bhattacharyya, Glen Ellyn, IL (US)

(73) Assignee: UOP LLC, Des Plaines, IL (US)

( * ) Notice: Subject to any disclaimer, the term of this patent is extended or adjusted under 35 U.S.C. 154(b) by 353 days.

(21) Appl. No.: 12/813,533

(22) Filed: Jun. 11, 2010

(65) Prior Publication Data

US 2011/0306809 A1    Dec. 15, 2011

(51) Int. Cl.
*C07C 2/66* (2006.01)

(52) U.S. Cl.
CPC ............... *C07C 2/66* (2013.01); *C07C 2529/70* (2013.01)
USPC .......................................... 585/467; 585/448

(58) Field of Classification Search
USPC ................................. 585/467, 448
See application file for complete search history.

(56) References Cited

U.S. PATENT DOCUMENTS

| | | |
|---|---|---|
| 4,028,227 A | 6/1977 | Gustafson |
| 5,273,644 A | 12/1993 | Wegerer |
| 5,453,554 A | 9/1995 | Cheng et al. |
| 5,557,024 A | 9/1996 | Cheng et al. |
| 5,602,290 A | 2/1997 | Fallon |
| 5,750,814 A | 5/1998 | Grootjans et al. |
| 5,756,872 A | 5/1998 | Smith, Jr. et al. |
| 5,856,607 A | 1/1999 | Kim |
| 6,002,058 A | 12/1999 | Hearn et al. |
| 6,051,521 A | 4/2000 | Cheng et al. |
| 6,313,362 B1 | 11/2001 | Green et al. |
| 6,504,071 B2 | 1/2003 | Zhang et al. |
| 6,652,737 B2 * | 11/2003 | Touvelle et al. ............... 208/137 |
| 6,783,659 B2 | 8/2004 | Porter et al. |
| 6,790,342 B1 | 9/2004 | Porter et al. |
| 6,995,295 B2 | 2/2006 | Clark et al. |
| 7,019,185 B2 | 3/2006 | Dandekar et al. |
| 7,038,100 B2 | 5/2006 | Dandekar et al. |
| 7,071,369 B2 | 7/2006 | Pohl |
| 7,074,978 B2 | 7/2006 | Pohl |
| 7,091,390 B2 | 8/2006 | Jan et al. |
| 7,259,282 B2 | 8/2007 | Hildreth et al. |
| 7,268,267 B2 | 9/2007 | Jan et al. |
| 7,297,829 B2 | 11/2007 | Dandekar et al. |
| 7,393,988 B2 | 7/2008 | Hildreth et al. |
| 7,425,659 B2 | 9/2008 | Clark |
| 7,524,467 B2 | 4/2009 | Pohl |
| 7,569,739 B2 | 8/2009 | Dandekar et al. |
| 7,608,745 B2 | 10/2009 | Hildreth et al. |
| 7,638,667 B2 | 12/2009 | Jan et al. |
| 7,652,181 B1 | 1/2010 | Schmidt et al. |
| 7,652,184 B2 | 1/2010 | Clark |
| 2006/0104896 A1* | 5/2006 | Drnevich et al. .......... 423/648.1 |
| 2006/0247479 A1 | 11/2006 | Barchha et al. |
| 2007/0255080 A1 | 11/2007 | Hildreth et al. |
| 2008/0194890 A1 | 8/2008 | Brown |
| 2008/0242905 A1 | 10/2008 | Clark et al. |
| 2008/0242907 A1 | 10/2008 | Clark et al. |
| 2008/0281137 A1 | 11/2008 | Clark et al. |
| 2009/0036722 A1* | 2/2009 | Clark et al. ................... 585/449 |
| 2009/0112028 A1 | 4/2009 | Schultz |
| 2009/0281361 A1 | 11/2009 | Clark et al. |
| 2009/0286670 A1 | 11/2009 | Clark et al. |
| 2010/0048970 A1 | 2/2010 | Boyer et al. |

FOREIGN PATENT DOCUMENTS

CN           101352690 A      1/2009

OTHER PUBLICATIONS

U.S. Appl. No. 12/813,534, filed Jun. 11, 2010, Nicholas et al.
Coughlan, "Alkylation Reactions over Ion-exchanged Molecular Sieve Zeolite Catalysts", J. Chem. Soc., Faraday Trans. 1, 1983, 79, 327-342.
Fort, "Carbon-14 Rearrangement in the Alkylation of Benzene with [1-14C]Ethanol over ZSM-5 Catalyst", Journal of Catalysis 96, 357-362 (1985).

* cited by examiner

*Primary Examiner* — Thuan D Dang
(74) *Attorney, Agent, or Firm* — James C Paschall

(57) ABSTRACT

The process converts ethylene in a dilute ethylene stream and dilute benzene in an aromatic containing stream via alkylation to heavier hydrocarbons. The catalyst may be a zeolite such as UZM-8. The catalyst is resistant to feed impurities such as hydrogen sulfide, carbon oxides, and hydrogen and selectively converts benzene. At least 40 wt-% of the ethylene in the dilute ethylene stream and at least 20 wt-% of the benzene in the dilute benzene stream can be converted to heavier hydrocarbons.

19 Claims, 3 Drawing Sheets

PROCESS FOR THE REDUCTION OF GASOLINE BENZENE CONTENT BY ALKYLATION WITH DILUTE ETHYLENE

BACKGROUND OF THE INVENTION

The field of the invention is a process for alkylating benzene in a naphtha stream with dilute ethylene. The alkylated product may be used as motor fuel.

Dry gas is the common name for the off-gas stream from a fluid catalytic cracking unit that contains all the gases with boiling points of ethane and lower. The off-gas stream is compressed to remove as much of the $C_3$ and $C_4$ gases as possible. Sulfur is also largely absorbed from the off-gas stream in a scrubber that utilizes an amine absorbent. The remaining stream is known as the FCC dry gas. A typical dry gas stream contains 5 to 50 wt-% ethylene, 10 to 20 wt-% ethane, 5 to 20 wt-% hydrogen, 5 to 20 wt-% nitrogen, about 0.05 to about 5.0 wt-% of carbon monoxide, 0.1 to about 5.0 wt-% of carbon dioxide and less than 0.01 wt-% hydrogen sulfide and ammonia with the balance being methane.

Currently, the FCC dry gas stream is sent to a burner as fuel gas. An FCC unit that processes 7,949 kiloliters (50,000 barrels) per day will burn about 181,000 kg (200 tons) of dry gas containing, for example, about 36,000 kg (40 tons) of ethylene as fuel per day. Because a large price difference exists between fuel gas and motor fuel products or pure ethylene it would appear economically advantageous to attempt to recover this ethylene. However, the dry gas stream contains impurities that can poison catalysts and is so dilute that ethylene recovery is not economically justified by gas recovery systems.

There is need for utilization of dilute ethylene in refinery streams.

Catalytic reforming is a well-established hydrocarbon conversion process employed in the petroleum refining industry for improving the octane quality of hydrocarbon feedstocks, the primary product of reforming being motor gasoline. In catalytic reforming, a naphtha feedstock is admixed with a recycle stream comprising hydrogen and contacted with catalyst in a reaction zone at temperatures of around 493° to 510° C. (920° to 950° F.) and moderate pressure around 1379 to 3792 kPa (200 to 550 psig). The usual feedstock for catalytic reforming is a petroleum fraction known as naphtha and having an initial boiling point of about 46° C. (115° F.) and an end boiling point of about 204° C. (400° F.).

The catalytic reforming process is particularly applicable to the treatment of straight run gasoline comprised of relatively large concentrations of naphthenic and substantially straight chain paraffinic hydrocarbons, which are subject to aromatization through dehydrogenation and/or cyclization reactions. The catalyst "reforms" the molecular structures of the hydrocarbons contained in the raw naphtha by removing hydrogen and rearranging the structure of the molecules so as to improve the octane number of the naphtha. However, the increase in octane number also reduces the liquid volume of the naphtha as the specific gravity is increased. Because of the multiplicity of the compounds in the raw naphtha, the actual reactions which occur in catalytic reforming are numerous. However, some of the many resulting products are aryl or aromatic compounds, all of which exhibit high octane numbers. The aryl compounds produced depend upon the starting materials which in a refinery are controlled by the boiling range of the naphtha used and the crude oil source. The "reformed" product from a catalytic reforming process is commonly called reformate and is often separated into two fractions by conventional distillations, a light reformate having a boiling range of about 46° to 121° C. (115° to 250° F.) and a heavy reformate having a boiling range of about 121° to 204° C. (250° to 400° F.). The aryl compounds in each fraction are thus dependent upon their boiling points. The lower boiling or lighter aryl compounds, e.g., benzene, toluene and xylenes, are contained in the light reformate, and higher boiling aryl compounds are contained in the heavy reformate.

The concentration of benzene in gasoline is now being regulated by the American government. The Mobil Source Air Toxics regulation (MSAT II) requires that the average benzene level in gasoline produced by a refiner be lower than 0.62 vol-% with a maximum of 1.3 vol-% in gasoline produced at any one refinery. Benzene is commonly produced at levels higher than this by reforming processes and FCC processes. As reformate and the naphtha streams from the FCC unit are two of the largest sources of gasoline in a refinery, benzene reduction strategies have to be used.

Currently, benzene is commonly sent to a saturation unit to reduce benzene to cyclohexane. However, this process utilizes at least three moles of hydrogen for every mole of benzene converted and there is an octane loss associated with the conversion of benzene to cyclohexane. Methods for the reduction of benzene in gasoline without loss of octane or use of hydrogen are necessary.

The alkylation of concentrated benzene streams with concentrated ethylene streams is known. Alkylation typically involves the use of clean ethylene streams because alkylation catalysts are susceptible to feed impurities. Additionally, dilute ethylene is little used as an oligomerization feedstock because of its much lower reactivity relative to higher olefins. Benzene streams fed to alkylation reactors are also concentrated because of concern that heavier aromatics will preferentially alkylate, thereby requiring the use of a large excess of ethylene before reducing the benzene concentration and producing undesirable polyalkylated benzene.

Definitions

The following definitions shall be applicable throughout this document.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "column" means a distillation column or columns for separating one or more components of different volatilities based on boiling point differential. A column may have a reboiler on its bottom and a condenser on its overhead. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feed to a column may be preheated. The top pressure is the pressure of the overhead vapor at the outlet of the column. The bottom temperature is the liquid bottom outlet temperature. Overhead lines and bottoms lines refer to the net lines from the column downstream of the reflux or reboil to the column.

As used herein, the term "a component-rich stream" means that the rich stream coming out of a vessel has a greater concentration of the component than the feed to the vessel.

As used herein, the term "a component-lean stream" means that the lean stream coming out of a vessel has a smaller concentration of the component than the feed to the vessel.

The term "$C_x$" is to be understood to refer to molecules having the number of carbon atoms represented by the subscript "x". Similarly, the term "$C_x-$" refers to molecules that contain less than or equal to x and preferably x and less carbon atoms. The term "$C_x+$" refers to hydrocarbons with more than or equal to x and preferably x and more carbon atoms.

SUMMARY OF THE INVENTION

We have found that dilute benzene in aromatic containing streams such as reformate or FCC light naphtha can be alkylated over zeolitic catalysts with ethylene in dilute ethylene streams, such as an FCC dry gas stream. The heavier hydrocarbons can be separated and blended in the gasoline and diesel pools. We have found most zeolitic catalysts that are suitable for alkylation of benzene with light olefins quickly deactivate in dilute ethylene streams. Neither the dilute nature of the ethylene, nor the impurities present substantially affect a catalyst comprising UZM-8. Additionally, conversion of benzene by alkylation with ethylene is as high as toluene and greater than heavier aromatics with UZM-8 catalyst. Consequently, dilute benzene in a naphtha stream such as reformate can be alkylated with dilute ethylene in an FCC dry gas stream to provide a liquid fuel product which is reduced in benzene concentration and easy to separate from the unconverted gas stream. The unconverted gas can then be burned as fuel gas, but with the more valuable ethylene recovered as gasoline range hydrocarbons.

Advantageously, the process can enable utilization of dilute ethylene in a stream and in the presence of feed impurities that can be catalyst poisons.

Advantageously, the process can enable reduction of the concentration of dilute benzene in a naphtha stream without utilizing hydrogen or reducing the liquid volume or the octane value of the naphtha stream even in the presence of heavier aromatic hydrocarbons.

In an embodiment, the invention comprises a process for alkylating benzene with ethylene comprising providing a dilute ethylene stream comprising between about 5 and about 50 wt-% ethylene. A benzene stream comprising at least about 3 wt-% toluene and at least about 20 wt-% paraffins is provided. The dilute ethylene stream and the benzene stream are contacted with an alkylation catalyst comprising UZM-8. Lastly, at least 20% of the benzene in the feed stream is converted to alkylbenzene.

In a further embodiment, the invention comprises a process for alkylating benzene with ethylene comprising contacting cracking catalyst with a hydrocarbon feed stream to crack hydrocarbons to cracked product hydrocarbons having lower molecular weight and deposit coke on the cracking catalyst to provide coked cracking catalyst. The coked cracking catalyst is separated from the cracked products. Oxygen is added to the coked cracking catalyst and coke on the coked cracking catalyst combusted with oxygen to regenerate the cracking catalyst. The cracked products are separated to obtain a dilute ethylene stream comprising between about 5 and about 50 wt-% ethylene. A benzene stream comprising at least about 3 wt-% toluene and at least about 20 wt-% paraffins is provided. The dilute ethylene stream and the benzene stream are contacted with an alkylation catalyst comprising UZM-8. At least 20% of the benzene in the feed stream is converted to alkylbenzene.

In a still further embodiment, the invention comprises a process for alkylating benzene with ethylene comprising providing a dilute ethylene stream comprising between about 5 and about 50 wt-% ethylene. A naphtha stream is contacted with a reforming catalyst to provide a reformate benzene stream comprising at least about 3 wt-% toluene and at least about 20 wt-% paraffins. The dilute ethylene stream and the benzene stream are contacted with an alkylation catalyst comprising UZM-8. At least 20% of the benzene in the feed stream is converted to alkylbenzene.

Additional features and advantages of the invention will be apparent from the description of the invention, the drawings and claims provided herein.

DETAILED DESCRIPTION

The present invention may be applied to any hydrocarbon stream containing ethylene and, preferably, a dilute proportion of ethylene. A suitable, dilute ethylene stream may typically comprise between about 5 and about 50 wt-% ethylene. An FCC dry gas stream is a suitable dilute ethylene stream. Other dilute ethylene streams may also be utilized in the present invention such as coker dry gas streams. Because the present invention is particularly suited to FCC dry gas, the subject application will be described with respect to utilizing ethylene from an FCC dry gas stream.

The present invention may also be applied to any hydrocarbon stream containing benzene and, preferably, a dilute proportion of benzene. A suitable benzene stream may typically comprise between about 1 and about 50 wt-% benzene, at least about 3 wt-% toluene and at least about 20 wt-% paraffins. A reformate stream is a suitable benzene stream. Other benzene streams may also be utilized in the present invention such as FCC aromatic naphtha streams. Because the present invention is particularly suited to a reformate stream, the subject application will be described with respect to utilizing benzene from a reformate stream.

Figure 1:
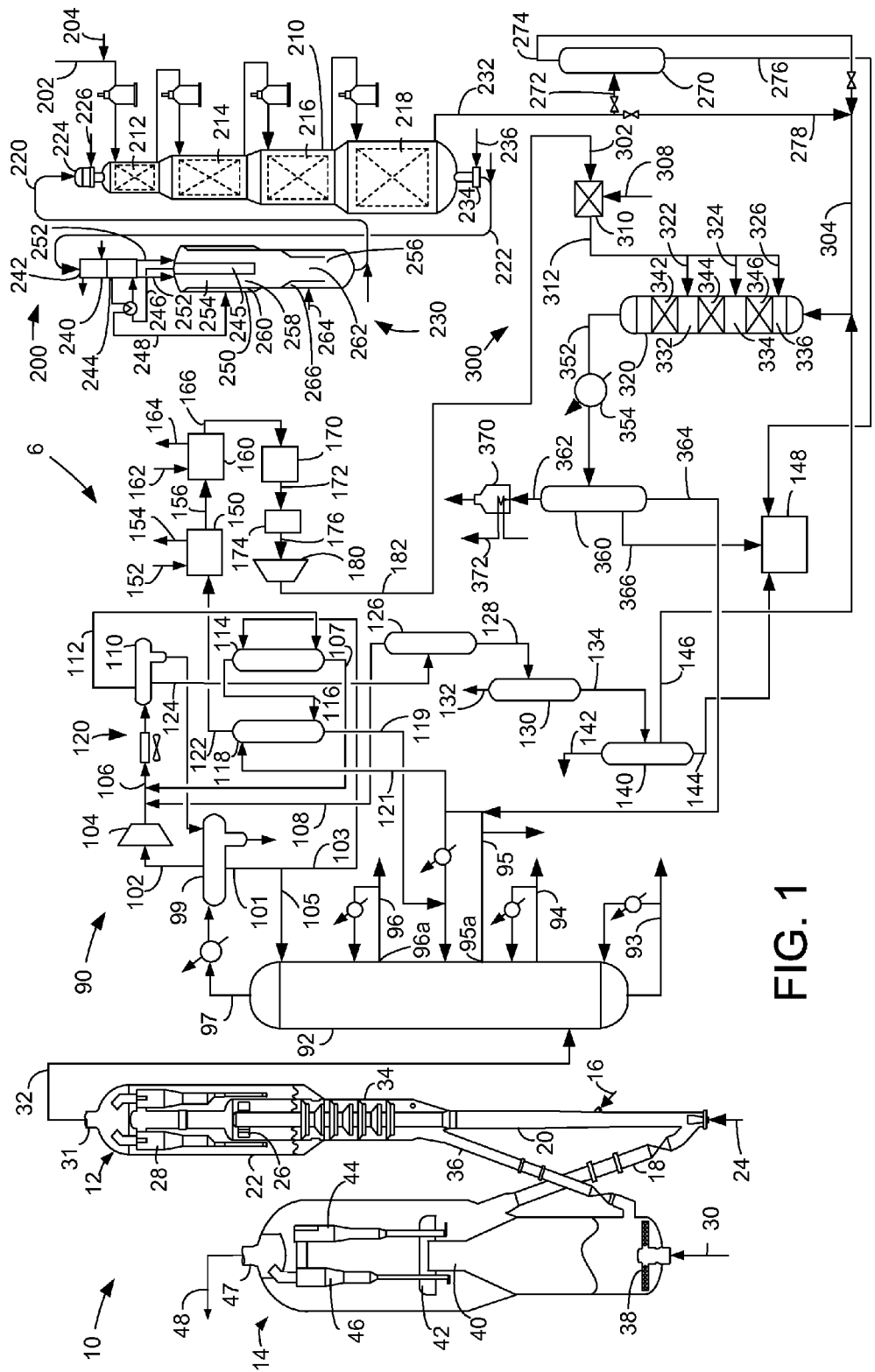
FIG. 1 is a schematic drawing of an FCC unit, a reforming unit and an alkylation unit.

Now turning to FIG. 1, wherein like numerals designate like components, the FIG. 1 illustrates a refinery complex 6 that generally includes an FCC unit 10 with a product recovery section 90, a reformer unit 200 and an alkylation unit 300.

The FCC unit 10 includes a reactor 12 and a catalyst regenerator 14. Process variables typically include a cracking reaction temperature of 400° to 600° C. and a catalyst regeneration temperature of 500° to 900° C. Both the cracking and regeneration occur at an absolute pressure below 506 kPa (72.5 psia).

FIG. 1 shows a typical FCC reactor 12 in which a heavy hydrocarbon feed or raw oil stream 16 is contacted from a distributor with a regenerated cracking catalyst entering from a regenerated catalyst standpipe 18. This contacting may occur in a narrow riser 20, extending upwardly to the bottom of a reactor vessel 22. The contacting of feed and catalyst is fluidized by gas from a fluidizing line 24. In an embodiment, heat from the catalyst vaporizes the hydrocarbon feed or oil, and the hydrocarbon feed is thereafter cracked to lighter molecular weight hydrocarbon products in the presence of the catalyst as both are transferred up the riser 20 into the reactor vessel 22. Inevitable side reactions occur in the riser 20 leaving coke deposits on the catalyst that lower catalyst activity. The cracked light hydrocarbon products are thereafter separated from the coked cracking catalyst using cyclonic separators which may include a primary separator 26 and one or two stages of cyclones 28 in the reactor vessel 22. Gaseous, cracked products exit the reactor vessel 22 through a product outlet 31 to line 32 for transport to a downstream product recovery section 90. The spent or coked catalyst requires regeneration for further use. Coked cracking catalyst, after separation from the gaseous product hydrocarbons, falls into a stripping section 34 in which steam is injected through a nozzle to purge any residual hydrocarbon vapor. After the stripping operation, the coked catalyst is carried to the catalyst regenerator 14 through a spent catalyst standpipe 36.

FIG. 1 depicts a regenerator 14 known as a combustor. However, other types of regenerators are suitable. In the catalyst regenerator 14, a stream of oxygen-containing gas 30, such as air, is introduced through an air distributor 38 to contact the coked catalyst. Coke is combusted from the coked catalyst to provide regenerated catalyst and flue gas. The catalyst regeneration process adds a substantial amount of heat to the catalyst, providing energy to offset the endothermic cracking reactions occurring in the reactor riser 20. Catalyst and air flow upwardly together along a combustor riser 40 located within the catalyst regenerator 14 and, after regeneration, are initially separated by discharge through a disengager 42. Additional recovery of the regenerated catalyst and flue gas exiting the disengager 42 is achieved using first and second stage separator cyclones 44, 46, respectively within the catalyst regenerator 14. Catalyst separated from flue gas dispenses through diplegs from cyclones 44, 46 while hot flue gas relatively lighter in catalyst sequentially exits cyclones 44, 46 and exits the regenerator vessel 14 through flue gas outlet 47 in flue gas line 48. Regenerated catalyst is carried back to the riser 20 through the regenerated catalyst standpipe 18. As a result of the coke burning, the flue gas vapors exiting at the top of the catalyst regenerator 14 in line 48 contain CO, $CO_2$, $N_2$ and $H_2O$, along with smaller amounts of other species.

The product recovery section 90 is in downstream communication with the product outlet 31. In the product recovery section 90, the gaseous FCC product in line 32 is directed to a lower section of an FCC main fractionation column 92. The main column 92 is in downstream communication with the product outlet 31. Several fractions of FCC product may be separated and taken from the main column including a heavy slurry oil stream from the bottoms in line 93, a heavy cycle oil stream in line 94, a light cycle oil in line 95 taken from outlet 95a and a heavy naphtha stream in line 96 taken from outlet 96a. Any or all of lines 93-96 may be cooled and pumped back to the main column 92 to cool the main column typically at a higher location. Gasoline and gaseous light hydrocarbons are removed in overhead line 97 from the main column 92 and condensed before entering a main column receiver 99. The main column receiver 99 is in downstream communication with the product outlet 31, and the main column 92 is in upstream communication with the main column receiver 99.

An aqueous stream is removed from a boot in the receiver 99. Moreover, a condensed light naphtha stream is removed in line 101 while an overhead stream is removed in line 102. The overhead stream in line 102 contains gaseous light hydrocarbon which may comprise a dilute ethylene stream. A portion of the condensed light naphtha stream in line 101 may be refluxed back to the main fractionation column 92 in line 105 leaving a net condensed light naphtha stream in line 103. The streams in lines 101 and 102 may enter a vapor recovery section 120 of the product recovery section 90.

The vapor recovery section 120 is shown to be an absorption based system, but any vapor recovery system may be used including a cold box system. To obtain sufficient separation of light gas components, the gaseous stream in line 102 is compressed in compressor 104. More than one compressor stage may be used, and typically a dual stage compression is utilized to compress the gaseous stream in line 102 to between about 1.2 MPa to about 2.1 MPa (gauge) (180 to 300 psig). Three stages of compression may be advantageous to provide additional pressure at least as high as 3.4 MPa (gauge) (500 psig).

The compressed light hydrocarbon stream in line 106 is joined by $C_3+$ hydrocarbon liquid stream in a primary absorber bottoms line 107 and a $C_2-$ hydrocarbon stream in stripper overhead line 108, chilled and delivered to a high pressure receiver 110. An aqueous stream from the receiver 110 may be routed to the main column receiver 99. A gaseous first FCC product stream in line 112 comprising a dilute ethylene stream is routed to a unit that effects a separation between $C_3+$ and $C_2-$ hydrocarbons, which in this embodiment is a primary absorber 114. In the primary absorber 114 the dilute ethylene, first FCC product stream is contacted with a second FCC product stream comprising unstabilized gasoline from the main column receiver 99 in line 103 to effect a separation between $C_3+$ and $C_2-$ hydrocarbons. The separator for separating $C_3$ from $C_2$ hydrocarbons, which may be the primary absorber 114, is in downstream communication with the main column receiver 99. A liquid $C_3+$ stream in line 107 is returned to line 106 prior to chilling. An overhead of the primary absorber 114 comprising dry gas of predominantly $C_2-$ hydrocarbons with hydrogen sulfide, ammonia, carbon oxides and hydrogen is removed in the primary off-gas stream in line 116 to comprise a dilute ethylene stream. However, to concentrate the ethylene stream further and to recover heavier components line 116 may optionally be directed to a second unit that effects a separation between $C_3+$ and $C_2-$ hydrocarbons, which in this embodiment is a secondary absorber 118. In the secondary absorber, a circulating stream of light cycle oil in line 121 diverted from line 95 absorbs most of the remaining $C_5+$ and some $C_3$-$C_4$ material in the primary off-gas stream. The secondary absorber 118 is in downstream communication with the primary absorber 114. Light cycle oil from the bottom of the secondary absorber in line 119 richer in $C_3+$ material is returned to the main column 92 via the pump-around for line 95. An overhead of the secondary absorber 118 comprising dry gas of predominantly $C_2-$ hydrocarbons with hydrogen sulfide, ammonia, carbon oxides and hydrogen is removed in the secondary off-gas stream in line 122 to comprise a dilute ethylene stream. Both of the absorber columns 114 and 118 have no condenser or reboiler, but may employ pump-around cooling circuits.

Liquid from the high pressure receiver 110 in line 124 is sent to a stripper column 126. Most of the $C_2-$ is removed in the overhead of the stripper 126 and returned to line 106 via overhead line 108. The stripper column 126 has no condenser but receives cooled liquid feed in line 124. A liquid bottoms stream from the stripper 126 is sent to a debutanizer column 130 via line 128. An overhead stream in line 132 from the debutanizer comprises $C_3$-$C_4$ olefinic product while a bottoms stream in line 134 comprising stabilized gasoline may be further treated and sent to gasoline storage. In an embodiment, the bottoms stream in line 134 may be sent to a naphtha splitter column 140. Light naphtha may be recovered in an overhead line 142 from the naphtha splitter column 140 with a heavy naphtha stream recovered in bottoms line 144. An aromatic naphtha comprising benzene may be taken as a mid cut in line 146 in which case the naphtha splitter column 140 may be a dividing wall column. One or both of light and heavy naphtha streams in lines 142 and 144 may be taken to a gasoline distribution system 148. Only heavy naphtha stream in line 144 is shown going to gasoline distribution system 148 in FIG. 1 because the light naphtha stream in line 142 may be directed to processing separate from the heavy naphtha.

The dilute ethylene stream of the present invention may comprise an FCC dry gas stream comprising between about 5 and about 50 wt-% ethylene and preferably about 10 to about 30 wt-% ethylene. Methane will typically be the predominant component in the dilute ethylene stream at a concentration of between about 25 and about 55 wt-% with ethane being substantially present at typically between about 5 and about 45 wt-%. Between about 1 and about 25 wt-% and typically about 5 to about 20 wt-% of hydrogen and nitrogen each may be present in the dilute ethylene stream. Saturation levels of water may also be present in the dilute ethylene stream. The dilute ethylene stream in overhead line 116 may have no more than 3 wt-% and suitably no more than 1 wt-% propylene and typically no more than 25 wt-% and suitably no more than 15 wt-% $C_3+$ materials. If the secondary absorber 118 is used, the dilute ethylene stream in overhead line 122 may have no more than about 5 wt-% of $C_3+$ with typically less than 0.5 wt-% propylene. Besides hydrogen, other impurities such as hydrogen sulfide, ammonia, carbon oxides and acetylene may also be present in the dilute ethylene stream.

Impurities in a dry gas ethylene stream can poison an alkylation catalyst. Carbon dioxide and ammonia can attack acid sites on the catalyst. Hydrogen sulfide is known at times to deactivate zeolite catalyst. Acetylene can polymerize and gum up on the catalyst or equipment.

The primary off-gas stream in line 116 or secondary off-gas stream in line 122, comprising a dilute ethylene stream may be introduced into an optional amine absorber unit 150 to remove hydrogen sulfide to lower concentrations. An aqueous amine solution, such as comprising monoethanol amine or diethanol amine, is introduced via line 152 into absorber 150 and is contacted with the flowing off-gas stream to absorb hydrogen sulfide, and a hydrogen sulfide-rich aqueous amine absorption solution is removed from absorption zone 150 via line 154 and recovered and perhaps further processed.

An optionally hydrogen sulfide-lean, amine-treated dilute ethylene stream in line 156 may be introduced into an optional water wash unit 160 to remove residual amine carried over from the amine absorber 150 and reduce the concentration of ammonia and carbon dioxide in the dilute ethylene stream in line 156. Water is introduced to the water wash in line 162. The water in line 162 is typically slightly acidified to enhance capture of basic molecules such as the amine. An aqueous stream in line 164 rich in amine and potentially ammonia and carbon dioxide leaves the water wash unit 160 and may be further processed.

The optionally amine treated, optionally water washed dilute ethylene stream in line 166 may then be treated in an optional guard bed 170 to remove one or more of the impurities such as carbon monoxide, hydrogen sulfide and ammonia down to lower concentrations. The guard bed 170 may contain an adsorbent to adsorb impurities such as ammonia that may poison an alkylation catalyst. The guard bed 170 may contain multiple adsorbents for adsorbing more than one type of impurity. A typical adsorbent for adsorbing hydrogen sulfide is ADS-12, for adsorbing carbon monoxide is ADS-106 and for adsorbing ammonia is UOP MOLSIV 3A all available from UOP, LLC. The adsorbents may be mixed in a single bed or can be arranged in successive beds.

The optionally amine-treated, optionally water-washed and optionally adsorption-treated stream in line 172 may be dried in a dryer 174 to remove water down to below about 500 wppm water. Water can adversely affect alkylation catalyst.

A dilute ethylene stream in line 176 optionally amine treated, optionally water washed, optionally adsorption treated and optionally dried will typically have at least one of the following impurity concentrations: about 0.05 wt-% and up to about 5.0 wt-% of carbon monoxide and/or about 0.1 wt-% and up to about 5.0 wt-% of carbon dioxide, and/or at least about 1 wppm and up to about 500 wppm hydrogen sulfide and/or at least about 1 and up to about 500 wppm ammonia, and/or at least about 5 and up to about 20 wt-% hydrogen. The type of impurities present and their concentrations will vary depending on the processing and origin of the dilute ethylene stream.

Line 176 carries the dilute ethylene stream to a compressor 180 if necessary to be pressured up to alkylation reactor pressure. The compressor 180 is in downstream communication with the main column 92, the product recovery section 90 and the product outlet 31. The compressor 180 may comprise one or more stages with interstage cooling. A heater may be required to bring the compressed stream up to reaction temperature. The compressed dilute ethylene gas stream is carried in line 182 to the alkylation unit 300. Line 182 feeds the dilute ethylene stream to the alkylation reactor unit 300. The alkylation reactor unit 300 may be in downstream communication with the compressor 180 and/or the first or second separators for separating $C_3$ hydrocarbons from $C_2$ hydrocarbons, which may be the primary or secondary absorbers 114 and 118, respectively. In an embodiment, no fractionation unit is in communication between the first separator or second separator for separating $C_3$ hydrocarbons from $C_2$ hydrocarbons and the alkylation reactor 320. Consequently, in an embodiment no fractionation unit is in communication between the primary absorber 114 or the secondary absorber 118 and the alkylation reactor 320. In this embodiment, the dilute ethylene stream may be subjected to separations based on adsorption or absorption, but no fractionation based on boiling point differential is conducted on the dilute ethylene stream which may comprise primary or secondary off-gas between the primary absorber 114 and/or secondary absorber 118 and the alkylation reactor 320. This embodiment stands in contradistinction to conventional belief which held that a dilute ethylene dry gas stream required fractionation such as in a demethanizer column to remove lighter components before the ethylene could sustain an alkylation reaction with benzene. The obviation of a demethanizer column results in substantial operating and capital savings.

Turning to the reforming unit 200, naphtha feedstock stream in line 202 is admixed with a stream comprising hydrogen from line 204, heated and contacted with catalyst in a reforming reactor 210 to produce a reformate. Desirably, the reforming reactor 210 is a moving bed reactor that receives regenerated catalyst through a line 220 and discharges spent catalyst through a line 222 to a regeneration zone 230 assisted by fluidized inert gas. Catalyst flows from the top to the bottom of the stacked reactor 210, passing first through a reduction zone 224, in which a hydrogen-rich gas from line 226 contacts and reduces the oxidized catalyst particles. From there, catalyst flows through multiple reaction zones in which naphtha feed contacts the catalyst particles. The reforming reactor 210 can comprise a stacked reactor arrangement, which can include a plurality of reactions zones. Each reaction zone has a catalyst bed in the stacked reactor 210 to permit continuous or intermittent flow of the catalyst particles from the top reaction zone 212 through second and third reaction zones 214 and 216, respectively, to a final zone 218. Effluent from the first through third reaction zones 212-216 may be withdrawn, heated and returned to the subsequent reaction zone 214-218, respectively. More or less catalyst beds can be used. A reformate product stream may be withdrawn in line 232 from the final reaction zone 218. A lower retention chamber 234 at the bottom of the stacked reactor 210 receives spent catalyst. A purging fluid preferably comprising hydrogen enters lower retention chamber 234 from a line 236 at a rate that purges hydrocarbons from the catalyst particles in lower retention chamber 234.

The usual feedstock for catalytic reforming is a petroleum fraction known as naphtha and having an initial boiling point of about 46° C. (115° F.) and an end boiling point of about 204° C. (400° F.). The catalytic reforming process is particularly applicable to the treatment of straight run naphtha comprised of relatively large concentrations of naphthenic and substantially straight chain paraffinic hydrocarbons, which are subject to aromatization through dehydrogenation and/or cyclization reactions. In reforming, dehydrogenation of cyclohexanes and dehydroisomerization of alkylcyclopentanes yield aromatics, dehydrogenation of paraffins yields olefins, dehydrocyclization of paraffins and olefins yields aromatics, isomerization of n-paraffins and alkylcycloparaffins yield cyclohexanes, substituted aromatics are isomerized and paraffins are hydrocracked.

A catalytic reforming reaction is normally effected in the presence of catalyst particles comprised of one or more Group VIII noble metals such as platinum, iridium, rhodium, palladium, and a halogen combined with a porous carrier, such as a refractory inorganic oxide. The halogen is normally chloride. Alumina is a commonly used carrier. The preferred alumina materials are known as the gamma, eta and theta alumina with gamma and eta alumina giving the best results. An important property related to the performance of the catalyst is the surface area of the carrier. Preferably, the carrier will have a surface area of from 100 to about 500 m$^2$/g. The particles are usually spheroidal and have a diameter of from about 1/16th to about 1/8th inch (1.5-3.1 mm), though they may be as large as 1/4th inch (6.35 mm). During the course of a reforming reaction, catalyst particles become deactivated as a result of mechanisms such as the deposition of coke on the particles; that is, after a period of time in use, the ability of catalyst particles to promote reforming reactions decreases to the point that the catalyst is no longer useful. The catalyst must be reconditioned, or regenerated, before it can be reused in a reforming process.

The regeneration zone 230 regenerates catalyst and recycles it to line 220. Spent catalyst particles containing coke deposits flow from the lower retention chamber 234 of the stacked reactor 210 through a lift conduit 222 into a disengaging vessel 240 in the regeneration zone 230. The disengaging vessel 240 may comprise two sections. In an upper section 242, an elutriation fluid enters upper section 242 at a rate that separates broken or chipped catalyst particles and catalyst fines from the whole catalyst particles which exit the bottom of the disengaging vessel 240. The catalyst chips and fines pass out of the upper section 242 with the elutriation fluid which may be filtered and recycled to the upper section 242. In the lower section 244, elutriated catalyst is contacted with cooled flue gas from line 246 to adsorb chlorines and hydrogen chloride onto the catalyst. The flue gas in line 246 may be heat exchanged with dechlorinated flue gas in line 248 from the lower section 244 to cool it into an adsorptive condition before it is fed to the lower section 244. Catalyst passes from the lower section 244 into the catalyst regenerator 250 via lines 252

The catalyst regenerator 250 comprises a combustion section 254 and a conditioning section 256. In the combustion section, catalyst descends in an inner annular chamber 258 which may comprise concentric screens impermeable to catalyst passage. Dechlorinated flue gas recycled in line 248 is heated by heat exchange with flue gas in line 246 and fed to an outer annular chamber 260. Recycled flue gas passes from outer annular chamber 260 through an outer screen into the inner annular chamber 258 to heat the catalyst therein. Gases used in the conditioning section 256 comprising oxygen and chlorine ascending from the conditioning section also passes into the inner annular chamber 258 to combust coke deposits from the catalyst. Hot combustion gases exit the inner concentric screen into an inner pipe 245 and leave the combustion section 254 in line 246. Combusted catalyst descends into the conditioning chamber 256 into a central space 262 within an annular baffle. Air which may be enriched with oxygen and mixed with chlorine is fed in line 264 to a lower annular chamber 266 outside of the annular baffle and passes into the central space 262 in contact with the catalyst to disperse the metal on the catalyst. Regenerated catalyst exits the conditioning section 256 and is lifted in line 220 back to the reforming reactor 210 assisted by fluidized gas.

A reformate splitter column 270 may be in downstream communication with the reforming reactor 210 and in communication between the reforming reactor 210 and an alkylation reactor via line 232. In this embodiment, the control valve on line 278 is at least partially closed, and the control valve on line 272 is at least partially open so line 272 is able to feed the reformate product stream from line 232 to reformate splitter column 270. Fractionation produces a light reformate stream in overhead line 274 which then feeds a benzene stream through an open control valve thereon into line 304 and alkylation reactor 320. The light reformate benzene stream can have about 20 to about 50 wt-% benzene, with at least 20 wt-% paraffins and the balance of at least 3 wt-% toluenes. In an embodiment, the light reformate benzene stream has a greater concentration of paraffins than benzene. The benzene stream preferably comprises at least about 4.0 wt-% benzene. The bottoms stream of heavy reformate in line 276 exiting a bottom half of the reformate splitter column 270 may bypass the alkylation reactor 320 and be routed to the gasoline distribution system 148 without communicating with the alkylation reactor 320.

Alternatively, the full reformate stream in line 232 may bypass the reformate splitter 270 or the reforming unit 200 may omit a reformate splitter column 270 altogether. In this embodiment, the control valve on lines 272 and 274 are closed, and the control valve on line 278 is at least partially open, so line 232 is able to feed the full reformate product stream to line 304 and the alkylation reactor 320. In this embodiment, the full reformate stream may be directed to an alkylation unit 300 in line 278. The reformate splitter may be omitted entirely. In this embodiment, no fractionation column is in communication between the reforming reactor 210 and the alkylation reactor 320. In this embodiment, the full reformate stream may be subjected to separations based on adsorption or absorption, but no fractionation based on boiling point differential is conducted on the reformate stream between the reforming reactor 210 and the alkylation reactor 320. This embodiment stands in contradistinction to conventional belief which held that a full reformate stream required fractionation such as in a reformate splitter column to remove heavy aromatics before the benzene could sustain an alkylation reaction with olefins. The obviation of a reformate splitter column results in substantial operating and capital savings.

The full reformate stream will comprise about 1 to about 10 wt-% benzene, about 3 to about 30 wt-% toluenes with the balance being at least about 20 wt-% paraffins and heavier aromatics. The full reformate stream comprises a greater concentration of aromatics with a molecular weight larger than benzene than a concentration of benzene. Specifically, the full reformate stream may have a greater concentration of aromatics with eight carbon atoms than a concentration of benzene. Additionally, the full reformate stream may have a greater concentration of paraffins than benzene.

Line 304 feeds the benzene stream to the alkylation unit 300. The alkylation unit 300 may be in downstream communication with the reformate splitter column 270. An alkylation reactor 320 preferably contains a fixed catalyst bed 342 and may contain a plurality of catalyst beds 342-46. The catalyst is preferably an UZM-8 zeolite bound with alumina.

In an embodiment, diolefins in the bottoms stream in the gaseous dilute ethylene stream in line 182 may optionally be delivered to be first reacted with a selective hydrogenation catalyst in selective hydrogenation zone 310, to selectively saturate diolefins without completely saturating them to paraffins. Suitable conditions for operation of a selective hydrogenation process include passing the dilute ethylene stream in line 302 in the gas phase and hydrogen from line 308 at molar ratio 0.5 to 5 moles hydrogen per mole of diolefin over a catalyst comprising at least one metal selected from the group formed by nickel, palladium and platinum, deposited on a support such as aluminum oxide, at a temperature of 20° to 200° C. (68° to 392° F.), a pressure of 689 to 3447 kPa(g) (100 to 500 psig), and a space velocity of 0.5 to 10 $hr^{-1}$. Two or more reaction zones may be used although only one is shown. Each reaction zone may employ a recycle (not shown) of reactor effluent to the reactor inlet with a ratio of recycle to ethylene feed stream ranging from 0 to 20. The residual diolefin content of such a process can be in the range 1 to 100 wppm, depending on the severity of the operation.

A dilute ethylene stream from selective hydrogenation reactor 310 in line 312 is injected into an alkylation reactor 320. In an aspect, a drier (not shown) on line 312 may be used to remove water to low concentrations which could affect the alkylation catalyst. Other guard beds are also contemplated to remove catalyst poisons such as removing ammonia or amines down to about 1 to about 500 wppm. One of the catalyst beds may serve as a guard bed to remove water and catalyst poisons. If a drier or a guard bed is used on the ethylene feed side in the alkylation unit 300, then one, part or both of drier 176 and adsorbent bed 170 may be omitted from the product recovery section 90. The dilute ethylene stream in line 312 has essentially the same composition as in line 114 or 122 with the exception of removed impurities. The dilute ethylene stream in line 312 optionally amine treated, optionally water washed, optionally adsorption treated and optionally dried may typically have at least one of the following impurity concentrations: about 0.05 wt-% and up to about 5.0 wt-% of carbon monoxide and/or about 0.1 wt-% and up to about 5.0 wt-% of carbon dioxide, and/or at least about 1 wppm and up to about 500 wppm hydrogen sulfide and/or at least about 1 and up to about 500 wppm ammonia and amines, and/or at least about 5 and up to about 20 wt-% hydrogen.

Although transalkylation reactions may occur in the alkylation reactor 320, alkylation reactions are predominant. The alkylation reactor is shown as an upflow reactor, but a downflow reactor may also be suitable. The stream in line 312 of dilute ethylene is injected into the alkylation reactor 320 in several lines 322, 324 and 326 into pre-bed spaces 332, 334 and 336 prior to entry into catalyst beds 342, 344 and 346, respectively. The catalyst beds 342, 344 and 346 contain alkylation catalyst to alkylate ethylene onto benzene to produce ethylbenzene and onto toluene to produce ethyltoluene. Other alkylation reactions occur to produce alkylbenzenes and alkylaromatics. The liquid benzene stream in line 304 is fed to the alkylation reactor 320 where it initially absorbs the dilute ethylene stream from the line 326 in the pre-bed space 336 and together enter the catalyst bed 346. The aromatic reformate feed stream in line 304 may also receive the FCC aromatic stream from line 146 before entering the alkylation reactor 320. Alternatively, if the naphtha splitter only provides two streams, one of these may feed line 304 with aromatic naphtha which is preferably light naphtha stream in line 142. Gaseous ethylene dissolves into the liquid reformate stream to alkylate with aromatic rings.

The effluent from the catalyst bed 346 is mixed with fresh dry gas comprising dilute ethylene from the line 324 in the pre-bed space 334 and together enter into the catalyst bed 344. The effluent from the catalyst bed 344 is mixed with fresh dry gas comprising dilute ethylene from the line 322 in the pre-bed space 332 and together enter into the catalyst bed 342. The process is repeated for the number of beds in the alkylation reactor 300. Although three catalyst beds are shown in the alkylation reactor 300, more or less beds and additional reactors may be suitable. Alkylation effluent from the alkylation reactor 320 is transported in an effluent line 352. A heat exchanger 354 may cool the effluent in the line 352 to a desirable temperature. The alkylation reactor effluent stream may be depressurized by passing through a pressure control valve or pressurized by passing through a pump, neither of which is shown.

A preferred alkylation catalyst of the present invention is described as follows. The preferred alkylation catalyst comprises an UZM-8 zeolite. One of the components of the catalyst support utilized in the present invention is alumina. The alumina source may be any of the various hydrous aluminum oxides or alumina gels such as alpha-alumina monohydrate of the boehmite or pseudo-boehmite structure, alpha-alumina trihydrate of the gibbsite structure, beta-alumina trihydrate of the bayerite structure, and the like. A particularly preferred alumina is available from Sasol North America Alumina Product Group under the trademark Catapal. This material is an extremely high purity alpha-alumina monohydrate (pseudo-boehmite) which after calcination at a high temperature has been shown to yield a high purity gamma-alumina. The zeolitic component of the catalyst is UZM-8 described in U.S. Pat. No. 6,756,030.

A suitable alkylation catalyst is prepared by mixing proportionate volumes of UZM-8 and alumina to achieve the desired zeolite-to-alumina ratio. In an embodiment, 70 wt-% UZM-8 and 30 wt-% alumina powder will provide a suitable support. In an embodiment, weight ratios other than 70-to-30 of UZM-8 to alumina may be suitable, ranging from 90 wt-% UZM-8 in content to 20 wt-% UZM-8 content with the balance alumina.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried.

The paste or dough may be prepared in the form of shaped particulates, with the preferred method being to extrude the dough through a die having openings therein of desired size and shape, after which the extruded matter is broken into extrudates of desired length and dried. A further step of calcination may be employed to give added strength to the extrudate. Generally, calcination is conducted in a stream of dry air at a temperature from about 260° C. (500° F.) to about 815° C. (1500° F.).

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as 40 μm; however, it is usually about 0.635 mm (0.25 inch) to about 12.7 mm (0.5 inch), preferably about 0.79 mm (1/32 inch) to about 6.35 mm (0.25 inch), and most preferably about 0.06 mm (1/24 inch) to about 4.23 mm (1/6 inch). Among the preferred catalyst configurations are cross-sectional shapes resembling that of a three-leaf clover, as shown, for example, in FIGS. 8 and 8A of U.S. Pat. No. 4,028,227. Preferred clover-shaped particulates are such that each "leaf" of the cross-section is defined by about a 270° arc of a circle having a diameter between about 0.51 mm (0.02 inch) and 1.27 mm (0.05 inch). Other preferred particulates are those having quadralobal cross-sectional shapes, including asymmetrical shapes, and symmetrical shapes such as in FIG. 10 of U.S. Pat. No. 4,028,227.

Since the reaction is conducted under at least partial liquid phase conditions, reaction pressure may be adjusted to maintain the ethylene at least partially in the liquid phase. Ethylene in the gas phase may also be suitable. Pressures can vary within a wide range of about 101 to about 13172 kPa (gauge) (1 to 1900 psig). As a practical matter the pressure normally is in the range between about 1379 and about 6985 kPa (gauge) (200 to 1000 psig) but usually is in a range between about 2069 and 4137 kPa (gauge) (300 and 600 psig). The temperature range appropriate for alkylation of the benzene with the ethylene is between about 100° and about 300° C. The ratio of aromatics to ethylene should be between about 1:10 and as high as about 10:1, with a ratio of 0.5 to 1.0 being preferred.

The dilute ethylene feed may be fed to the alkylation reactor 320 in the gas phase at a temperature between about 100° and about 300° C. The reaction takes place predominantly in the liquid phase at a WHSV 0.01 to 10 $hr^{-1}$ on ethylene basis. The gaseous ethylene may absorb into the liquid benzene stream for alkylation to occur. We have found, surprisingly, that despite the presence of impurities in the feed that poison the catalyst and dilute the ethylene in the feed, that at least about 40 wt-% and as much as about 75 wt-% of the ethylene in the feed stream alkylate with aromatic rings to convert to heavier alkylaromatic hydrocarbons.

The dilute benzene feed may be fed to the alkylation reactor 320 in the liquid phase at a temperature between about 100° and about 300° C. The reaction takes place predominantly in the liquid phase at a WHSV of 0.1 to 40 $hr^{-1}$ on benzene basis. We have found, surprisingly, that despite the presence of heavier aromatics and paraffins in the feed that dilute the benzene in the feed, that at least about 20 wt-%, suitably at least about 50 wt-% and as much as about 100 wt-% of the benzene in the feed stream convert to heavier alkylbenzene. Moreover, the conversion of benzene is at least about 80%, preferably at least about 90% and most preferably at least about 95% of the conversion of toluene. Even though the dilute benzene feed may have a higher concentration of aromatics having eight carbon atoms than the benzene concentration, the benzene undergoes greater conversion than the aromatics having eight carbon atoms. The benzene to olefin ratio may be between 0.2 and 4.0.

The catalyst remains stable despite the impure feed, but it can be regenerated upon deactivation. Suitable regeneration conditions include subjecting the catalyst, for example, in situ, to hot air at 500° C. for 3 hours. Activity and selectivity of the regenerated catalyst is comparable to fresh catalyst.

The alkylation product stream from the alkylation reactor in line 352 can be transported to an alkylation product fractionation column 360 which may be a simple flash drum but is preferably a fractionation column to separate a gaseous stream from a liquid stream. The alkylation product fractionation column 360 is in downstream communication with the alkylation reactor 320. The gaseous product stream in overhead line 362 comprising light gases such as hydrogen, methane, ethane, unreacted olefins and light impurities may be transported to a combustion unit 370 to generate steam in line 372. Alternatively, the gaseous product in overhead line 362 may be combusted to fire a heater (not shown) and/or to provide a source of flue gas to turn a gas turbine (not shown) to generate power. The overhead line 362 is in upstream communication with the combustion unit 370. The liquid bottoms stream comprising heavier hydrocarbons in line 364 from the alkylation product fractionation column 360 can be let down over a valve and recycled back to the product separation section 90 via LCO pump-around 95. Consequently, the main column 92 is in downstream and upstream communication with the alkylation reactor 320. The bottoms stream in line 364 is preferably recycled to the main column 92 at a location between the heavy naphtha outlet 96a and the light cycle oil outlet 95a. The recycle line 364 is in downstream communication with a bottom of the alkylation product fractionation column 360. Alternatively, the recycle line 364 feeds the light cycle oil pump-around line 95 or the heavy naphtha pump-around line 96. The recycle line 364 is in downstream communication with the alkylation reactor 320 and in upstream communication with the main column 92. Alternatively, the alkylation product in lines 364 may be transported to the gasoline distribution system 148 without recycling to the product separation zone 90.

A stream of naphtha range alkyl benzene with a smaller concentration of benzene than in line 304 which may be from a side cut in outlet line 366 may be recovered and delivered to the gasoline distribution system 148. The gasoline distribution system 148 may comprise piping to an outlet, to a dispenser for filling a tank for transportation or to a gasoline storage tank. The gasoline distribution system 148 is in downstream communication with the alkylation reactor 320. In an embodiment, the side cut stream in line 366 will have a larger flow rate than the bottoms stream in line 364, which may just be a drag stream.

EXAMPLES

The utility of the present invention will be demonstrated by the following examples.

Example 1

An extruded UZM-8 catalyst was synthesized by combining an UZM-8 powder with Si/Al ratio of 12, and pseudo-boehmite provided under the Catapal trademark. The pseudo-boehmite was peptized with nitric acid before mixture with the amorphous silica-alumina. The catalyst dough was extruded through 1.59 mm openings in a cylindrical die plate and broken into pieces prior to calcination at 550° C. The finished catalyst consisted of 70 wt-% UZM-8 and 30 wt-% alumina and had a surface area of 368 $m^2/g$.

Example 2

The catalyst of Example 1 was tested for benzene alkylation at 205° C., 3447 kPa (500 psig), 0.4 OWHSV (olefin weight hourly space velocity) and a liquid feed WHSV of 4.9 in a fixed bed operation over 10 mL of catalyst. The gas feed consisted of 23 mol-% $C_2H_4$ and 77 mol-% $CH_4$. The liquid feed consisted of 2.6 wt-% pentene, 6.4 wt-% $C_6H_6$, 30 wt-% n-heptane, 25 wt-% toluene, 18 wt-% aromatics having eight carbon atoms (C$_8$ aromatics), and 19 wt-% aromatics having nine carbon atoms (C$_9$ aromatics).

Of ethylene, 83% was converted, and 51% of benzene was converted. Toluene conversion was 49% while conversion of C$_8$ and C$_9$ aromatics was less than 20%. Selectivity to ethylbenzene was 5%, to ethyltoluenes was 25%, to diethylbenzenes was 6%, to other gasoline range compounds was 37% and to compounds boiling at greater than 225° C. was 27%.

After 13 hours, the temperature was increased to 236° C. At the 26 hour mark, the liquid feed WHSV was increased to 12.7. Under these conditions, the ethylene conversion was 83%, with benzene conversion of 32%, toluene conversion of 27% and C$_8$ and C$_9$ aromatic conversion of less than 15%. Selectivity was 4% to ethylbenzene, 17% to ethyltoluenes, 2.5% to diethylbenzenes, 53.5% to other gasoline range compounds and 23% to compounds boiling at greater than 225° C.

Figure 2:
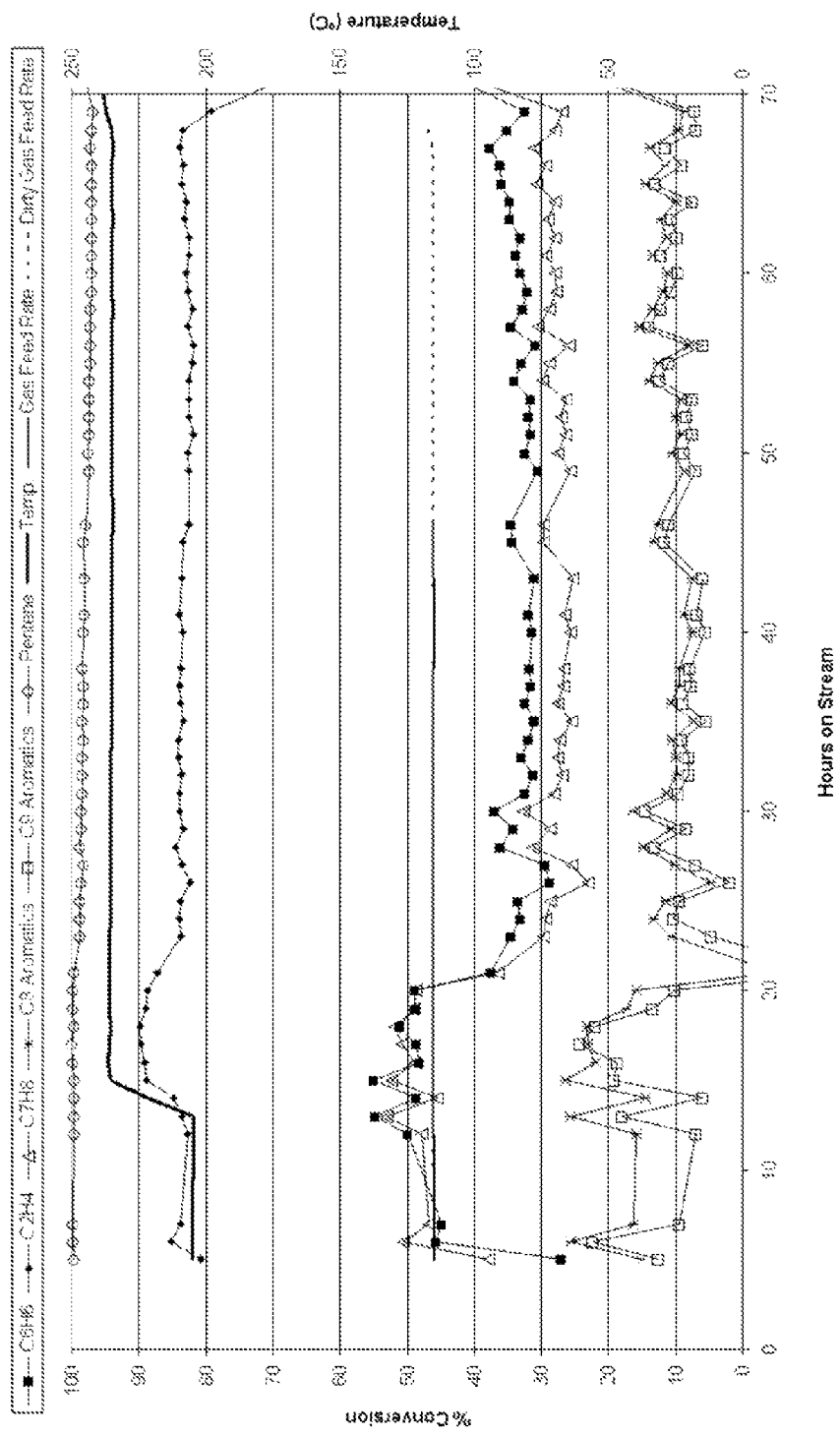
FIG. 2 is a graph of conversion and temperature over time.

At 46 hours on stream, the gas feed was changed to a blend representing an FCC dry gas composition containing 34 mol-% CH$_4$, 23 mol-% C$_2$H$_4$, 14 mol-% C$_2$H$_6$, 13 mol-% H$_2$, 13 mol-% N$_2$, 2 mol-% CO$_2$, 1 mol-% CO and 1 ppm H$_2$S. Conversions and selectivities did not change. This experiment is shown in FIG. 2.

Example 3

Figure 3:
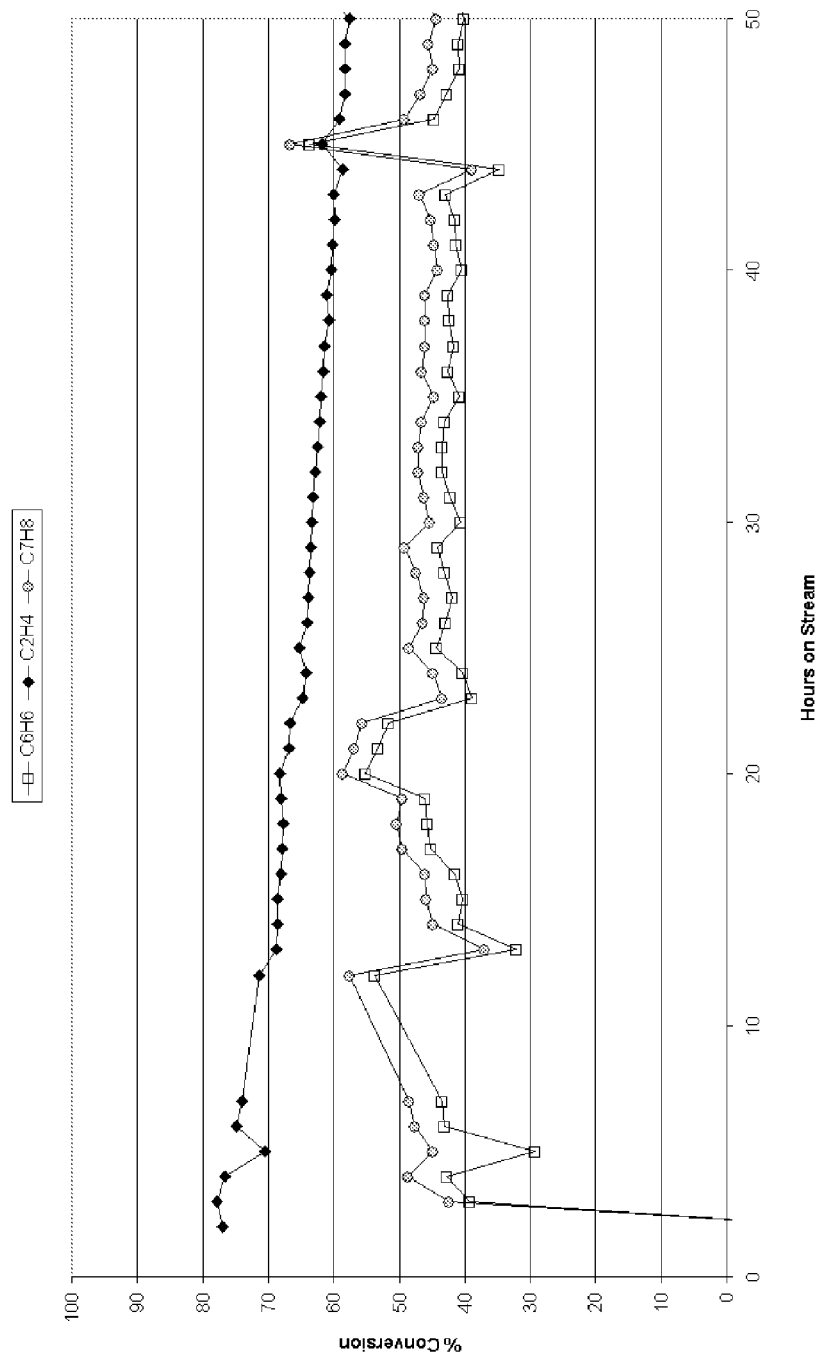
FIG. 3 is a graph of conversion over time.

The catalyst of Example 1 was tested for benzene alkylation at 205° C., 3447 kPa (500 psig), 0.8 OWHSV and a liquid feed WHSV of 7 in a fixed bed operation over 12 mL of catalyst. The gas feed consisted of 34 mol-% CH$_4$, 23 mol-% C$_2$H$_4$, 14 mol-% C$_2$H$_6$, 13 mol-% H$_2$, 13 mol-% N$_2$, 2 mol-% CO$_2$, 1 mol-% CO and 1 ppm H$_{25}$ resembling a dry gas feed. The liquid feed consisted of 39 wt-% benzene, 49 wt-% n-heptane and 12 wt-% toluene. Ethylene conversion ranged from 77% to 58% over 50 hours on stream with a constant 44% benzene conversion. Toluene conversion was 47%. Selectivity was 50-53% to ethylbenzene, 14-16% to ethyltoluenes, 17-19% to diethylbenzenes, 11-14% to other gasoline range compounds and 3% to compounds boiling at greater than 225° C. This experiment is shown in FIG. 3.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for alkylating benzene with ethylene comprising:
   providing a dilute ethylene stream comprising between about 5 and about 50 wt-% ethylene and between about 25 and about 55 wt-% methane;
   providing a benzene stream comprising at least about 3 wt-% toluene and at least about 20 wt-% paraffins, the benzene stream being a liquid benzene stream;
   contacting predominantly in the liquid phase the dilute ethylene stream further comprising at least about 1 wppm hydrogen sulfide and at least about 1 wppm ammonia and the liquid benzene stream with an alkylation catalyst comprising UZM-8; and
   converting at least 20% of the benzene in the liquid benzene stream to alkylbenzene wherein the conversion of benzene is at least 90% of the conversion of toluene.

2. The process of claim 1 wherein the benzene stream has a greater concentration of aromatics with a molecular weight greater than benzene than the concentration of benzene.

3. The process of claim 1 wherein the benzene stream comprises a higher concentration of aromatics having eight carbon atoms than benzene, but the benzene undergoes a greater conversion than the aromatics having eight carbon atoms.

4. The process of claim 1 wherein said benzene stream has a greater concentration of paraffins than benzene.

5. The process of claim 1 wherein said contacting step is performed in a fixed bed of said catalyst.

6. The process of claim 1 wherein said dilute ethylene stream includes at least one impurity selected from the group consisting of at least about 0.05 wt-% carbon monoxide, at least about 5 wt-% hydrogen and at least about 0.1wt-% carbon dioxide.

7. The process of claim 1 wherein said benzene stream is provided as a reformate stream from a reforming reactor.

8. The process of claim 7 wherein said reformate stream is not fractionated between said reforming reactor and said alkylation reactor.

9. The process of claim 1 wherein said dilute ethylene stream is provided from a first FCC product stream from an FCC reactor.

10. The process of claim 9 wherein said first FCC product stream is contacted with a second FCC product stream in an absorber to provide said dilute ethylene stream and said dilute ethylene stream is not fractionated between said absorber and said alkylation reactor.

11. The process of claim 1 wherein said dilute ethylene stream is fed to the reactor in the gas phase and the benzene stream is fed to the reactor in the liquid phase.

12. The process of claim 11 wherein said feed stream contacting step is performed at a WHSV 0.1 to 10 hr$^{-1}$ on ethylene basis.

13. The process of claim 1 wherein said dilute ethylene stream comprises between about 10 and about 30 wt-% ethylene.

14. The process of claim 1 wherein said benzene to olefin ratio is between 0.2 and 4.0.

15. The process of claim 1 wherein said benzene stream has at least 4.0 wt-% benzene.

16. A process for alkylating benzene with ethylene comprising:
   contacting cracking catalyst with a hydrocarbon feed stream to crack hydrocarbons to cracked product hydrocarbons having lower molecular weight and deposit coke on the cracking catalyst to provide coked cracking catalyst;
   separating said coked cracking catalyst from said cracked products;
   adding oxygen to said coked cracking catalyst;
   combusting coke on said coked cracking catalyst with oxygen to regenerate said cracking catalyst;
   separating said cracked products to obtain a dilute ethylene stream comprising between about 5 and about 50 wt-% ethylene, between about 0.05 wt-% and about 5.0 wt-% carbon monoxide and between about 25 and about 55 wt-% methane;
   providing a benzene stream comprising at least about 3 wt-% toluene and at least about 20 wt-% paraffins;

contacting predominantly in the liquid phase the dilute ethylene stream and the benzene stream with an alkylation catalyst comprising UZM-8; and converting at least 20% of the benzene in the benzene stream to alkylbenzene.

17. The process of claim 16 wherein said benzene stream is provided as a reformate stream from a reforming reactor and said reformate stream is not fractionated between said reforming reactor and said alkylation reactor.

18. A process for alkylating benzene with ethylene comprising:

providing a dilute ethylene stream comprising between about 5 and about 50 wt-% ethylene, between about 0.05 wt-% and about 5.0 wt-% carbon monoxide and between about 25 and about 55 wt-% methane;

contacting a naphtha stream with a reforming catalyst to provide a reformate benzene stream comprising at least about 3 wt-% toluene and at least about 20 wt-% paraffins;

contacting predominantly in the liquid phase the dilute ethylene stream and the benzene stream with an alkylation catalyst comprising UZM-8, the benzene stream being a liquid benzene stream; and converting at least 20% of the benzene in the liquid benzene stream to alkylbenzene.

19. The process of claim 16 wherein the contacted dilute ethylene stream further comprises at least about 1 wppm hydrogen sulfide and at least about 1 wppm ammonia.

* * * * *